(12) United States Patent
Li et al.

(10) Patent No.: US 8,308,645 B2
(45) Date of Patent: Nov. 13, 2012

(54) ULTRASONIC SCANHEAD

(75) Inventors: Pai-Chi Li, Taipei (TW); Jian-Hung Liu, Taipei (TW)

(73) Assignee: Li. Pai-Chi, Teipei (TW)

( * ) Notice: Subject to any disclaimer, the term of this patent is extended or adjusted under 35 U.S.C. 154(b) by 265 days.

(21) Appl. No.: 12/684,895

(22) Filed: Jan. 8, 2010

(65) Prior Publication Data
US 2011/0004103 A1 Jan. 6, 2011

(30) Foreign Application Priority Data
Jul. 1, 2009 (TW) .............................. 98122245 A

(51) Int. Cl.
*A61B 8/00* (2006.01)
(52) U.S. Cl. ........................................ 600/459; 600/437
(58) Field of Classification Search ................. 600/437, 600/459
See application file for complete search history.

(56) References Cited

U.S. PATENT DOCUMENTS

| 6,551,245 B1 * | 4/2003 | Irioka et al. .................... 600/444 |
| 7,255,678 B2 * | 8/2007 | Mehi et al. ..................... 600/446 |
| 7,322,098 B2 * | 1/2008 | Buitron et al. ................... 29/604 |

* cited by examiner

*Primary Examiner* — Long V. Le
*Assistant Examiner* — Katherine Fernandez
(74) *Attorney, Agent, or Firm* — Chun-Ming Shih

(57) ABSTRACT

An ultrasonic scanhead including an encoder, a pivot, a voice coil motor, and a transducer is provided. The encoder includes a fixed element and a rotary element. The rotary element is disposed at the fixed element and capable of rotating about a first axis. The pivot is through the encoder and capable of rotating with the rotary element. The pivot extends along a second axis and has a first end and a second end opposite to the first end. The voice coil motor includes a stator and a mover. The first end of the pivot is connected to the mover. The mover is capable of moving linearly along a third axis. The first axis, the second axis, and the third axis are substantially perpendicular to each other. The transducer is disposed at the second end of the pivot and capable of emitting an ultrasonic wave.

5 Claims, 9 Drawing Sheets

ULTRASONIC SCANHEAD

CROSS-REFERENCES

This application claims priority to Taiwan application No. 098122245 filed on Jul. 1, 2009.

BACKGROUND

1. Field of the Invention

The invention relates to a scanhead and in particular, to an ultrasonic scanhead.

2. Description of the Prior Art

A transducer of an ultrasonic scanhead is capable of transforming electrical signals into ultrasonic impulse signals and transmitting the ultrasonic impulse signals. When the transducer of the ultrasonic scanhead attaches to a human skin, the transducer transmits the ultrasonic impulse signals into the human body. Because different kinds of body tissues reflect the ultrasonic impulse signals transmitted into the human body in different degrees such that an image having characteristic information is received by the transducer. The transducer further transforms the received ultrasonic impulse signals into electrical signals and transmits the electrical signals into a computer for further calculation. By means of the abovementioned procedures, related image is displayed on a display device of the computer.

A conventional art of the ultrasonic scanhead has been disclosed in U.S. Pat. No. 7,255,678. However, in the conventional art, an encoder, and a transducer are located at opposite ends of a pivot of the ultrasonic scanhead, so the size of the conventional ultrasonic scanhead is relatively large. In addition, in the conventional art, a torque motor of the ultrasonic scanhead drives the pivot to rotate back and forth. However, during operation of the torque motor, shortcomings such as stagnation behavior, force ripple, and cogging force arise. Moreover, the transducer of the conventional ultrasonic scanhead can not be replaced. For the abovementioned reasons, it is necessary to improve the conventional ultrasonic scanhead.

BRIEF SUMMARY

The invention is directed to provide an ultrasonic scanhead, wherein a pivot of the ultrasonic scanhead is through an encoder such that the size of the ultrasonic scanhead is relatively small.

Other objects and advantages of the invention may be further comprehended through the technical features disclosed in the invention.

In order to achieve one or part of or all the objectives or other objectives, an embodiment of the invention provides an ultrasonic scanhead including an encoder, a pivot, a voice coil motor, and a transducer. The encoder includes a fixed element and a rotary element. The rotary element is disposed at the fixed element and capable of rotating about a first axis. The pivot is through the encoder and capable of rotating with the rotary element. The pivot extends along a second axis and has a first end and a second end opposite to the first end.

The voice coil motor includes a stator and a mover. The first end of the pivot is connected to the mover. The mover is capable of moving linearly along a third axis and moving relatively to the stator. The first axis, the second axis, and the third axis are substantially perpendicular to each other. The transducer is disposed at the second end of the pivot and capable of emitting an ultrasonic wave.

In one embodiment of the invention, the transducer is detachably disposed at the second end of the pivot. In addition, the transducer includes a screw thread and the transducer is fixed to the second end of the pivot via the screw thread by means of a rotation manner.

In one embodiment of the invention, the ultrasonic scanhead further includes an outer cover. The outer cover includes an outer cover body and a front cover. The encoder, the pivot, the voice coil motor, and the transducer are disposed in the outer cover. The front cover is disposed at an opening of the outer cover body and the transducer is located within the front cover.

In one embodiment of the invention, the ultrasonic scanhead further includes a connecting element. The first end of the pivot is connected to the connecting element and the connecting element clasps the mover.

The embodiment or the embodiments of the invention may have at least one of the advantages. In the embodiment of the invention, because the pivot of the ultrasonic scanhead is through the encoder, as compared to the conventional art, the size of the ultrasonic scanhead of the embodiment of the invention is relatively small. In addition, because the voice coil motor of the ultrasonic scanhead of the embodiment of the invention drives the pivot reciprocating, as compared to the conventional art, the voice coil motor operates smoothly without force ripple and cogging force. Moreover, because the transducer of the ultrasonic scanhead of the embodiment of the invention is detachably disposed at the second end of the pivot, as compared to the conventional art, it is convenient for a user to make a replacement for the transducer of the ultrasonic scanhead of the embodiment of the invention.

Other objectives, features and advantages of the present invention will be further understood from the further technology features disclosed by the embodiments of the present invention wherein there are shown and described preferred embodiments of this invention, simply by way of illustration of modes best suited to carry out the invention.

BRIEF DESCRIPTION OF THE DRAWINGS

The accompanying drawings are included to provide a further understanding of the embodiments of the invention, and are incorporated in and constitute part of this specification. The drawings illustrate embodiments of the invention and, together with the description, serve to explain the principles of the invention.

DETAILED DESCRIPTION

In the following detailed description of the embodiments, reference is made to the accompanying drawings which form a part hereof, and in which is shown by way of illustration specific embodiments in which the invention may be practiced. In this regard, directional terminology, such as "top," "bottom," "front," "back," etc., is used with reference to the orientation of the Figure(s) being described. The components of the invention can be positioned in a number of different orientations. As such, the directional terminology is used for purposes of illustration and is in no way limiting. On the other hand, the drawings are only schematic and the sizes of components may be exaggerated for clarity. It is to be understood that other embodiments may be utilized and structural changes may be made without departing from the scope of the invention. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. Similarly, the terms "facing," "faces" and variations thereof herein are used broadly and encompass direct and indirect facing, and "adjacent to" and variations thereof herein are used broadly and encompass directly and indirectly "adjacent to". Therefore, the description of "A" component facing "B" component herein may contain the situations that "A" component facing "B" component directly or one or more additional components is between "A" component and "B" component. Also, the description of "A" component "adjacent to" "B" component herein may contain the situations that "A" component is directly "adjacent to" "B" component or one or more additional components is between "A" component and "B" component. Accordingly, the drawings and descriptions will be regarded as illustrative in nature and not as restrictive.

Figure 1:
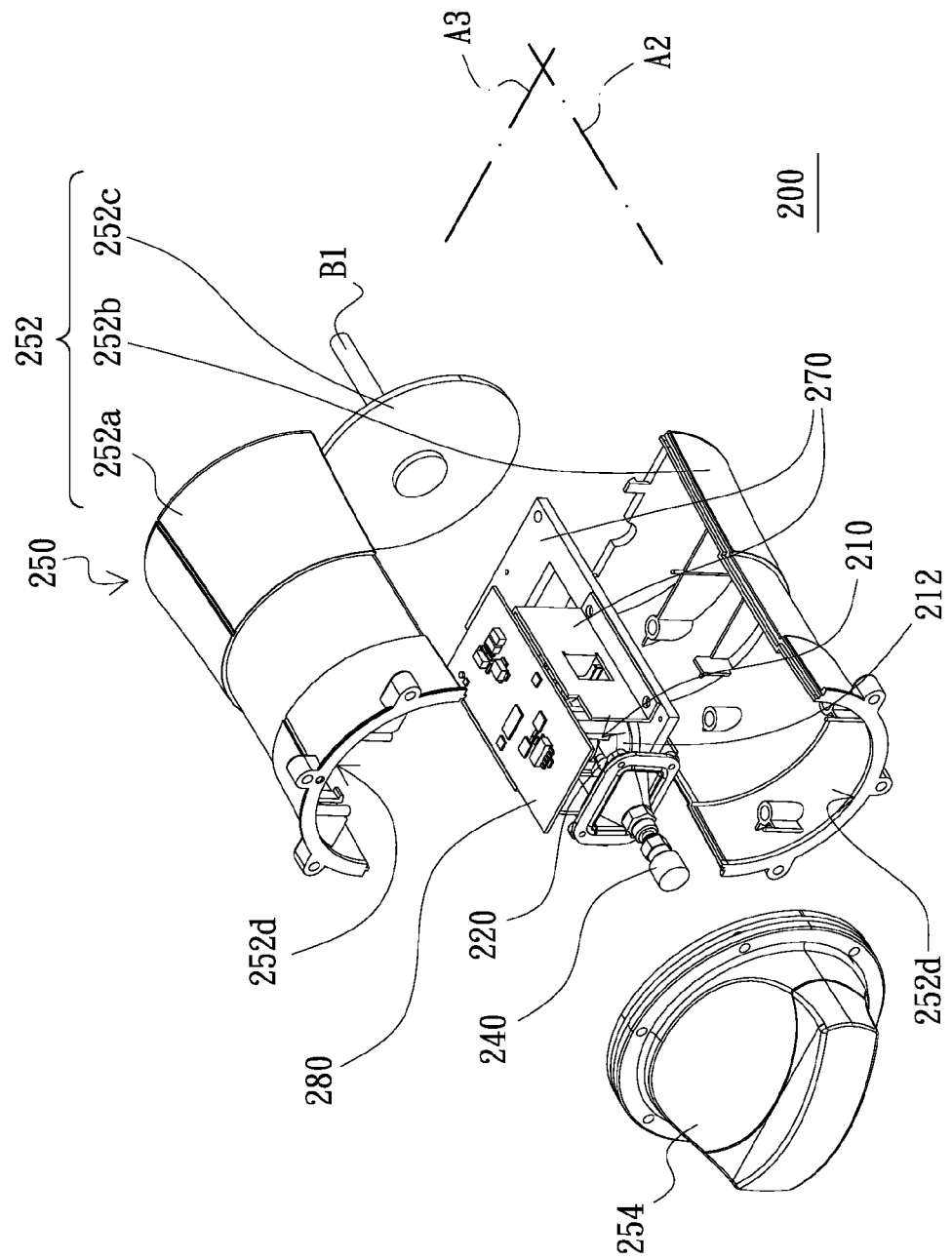
FIG. 1 is a partly exploded three-dimensional schematic view of an ultrasonic scanhead according to an embodiment of the invention.
Figure 2:
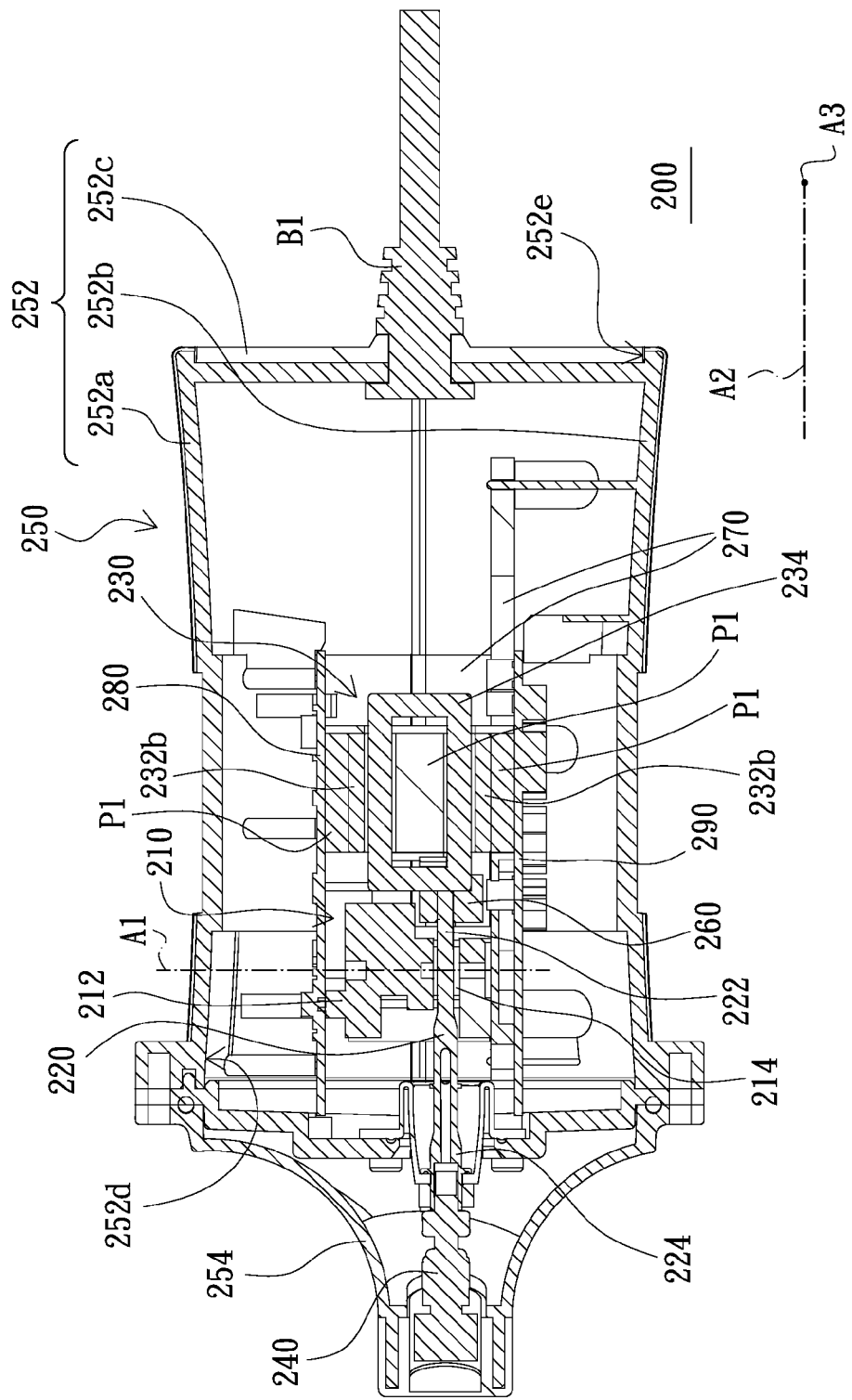
FIG. 2 is a schematic cross-sectional view of the ultrasonic scanhead of FIG. 1 which is assembled.
Figure 3:
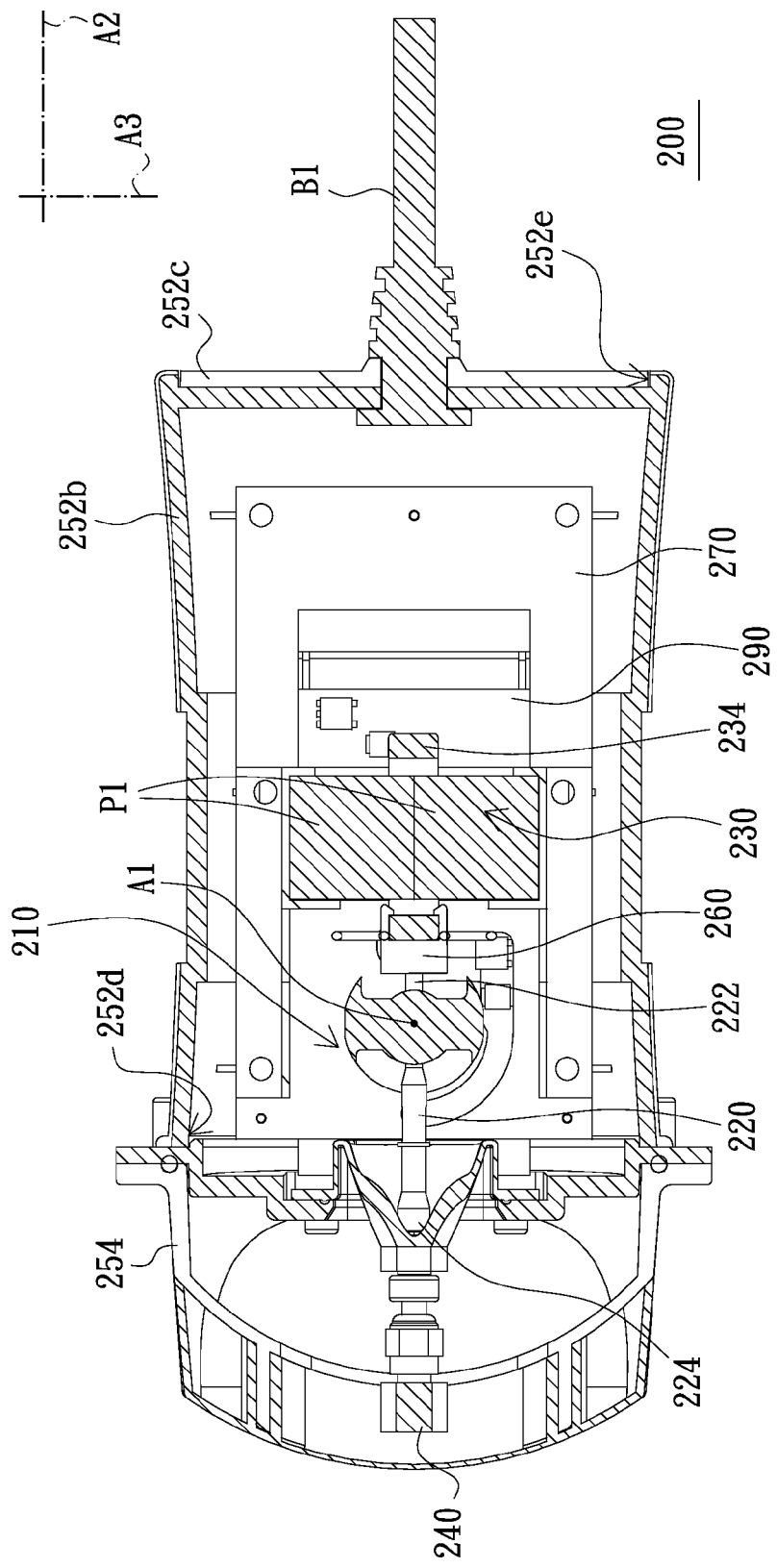
FIG. 3 is another schematic cross-sectional view of the ultrasonic scanhead of FIG. 1 which is assembled.
Figure 4:
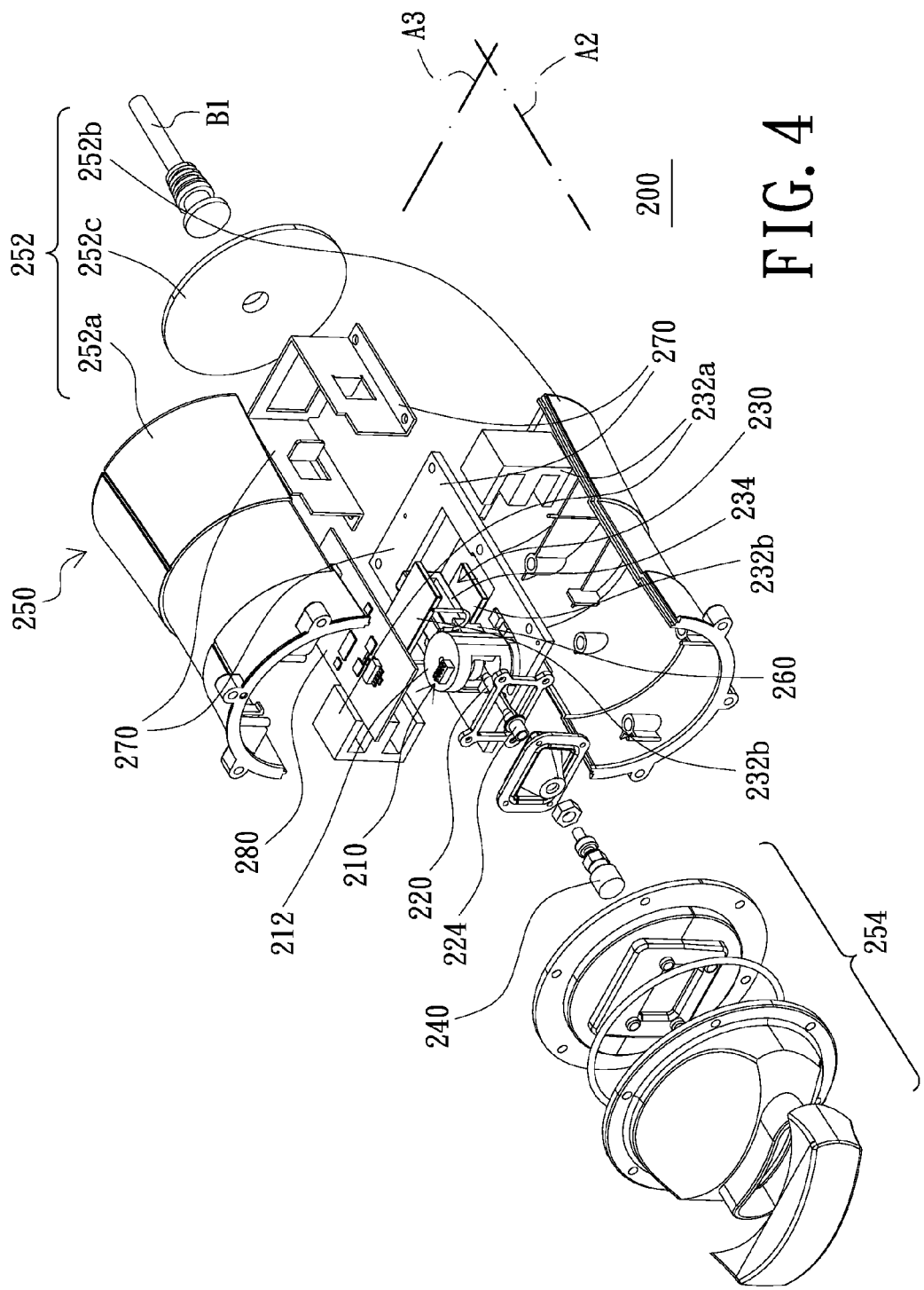
FIG. 4 is a schematic three-dimensional view of the ultrasonic scanhead of FIG. 1 which is exploded in detail.
Figure 5:
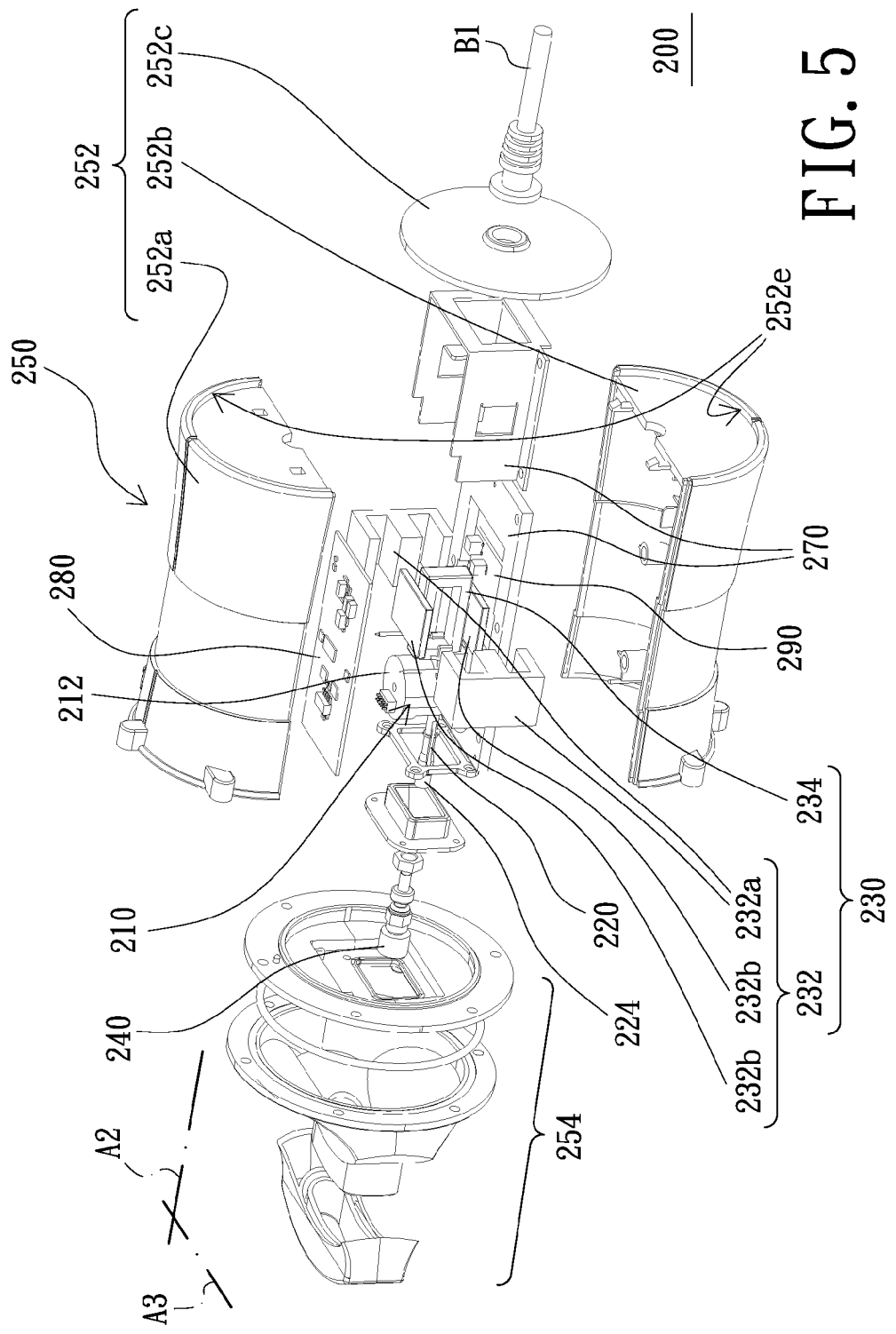
FIG. 5 is another schematic three-dimensional view of the ultrasonic scanhead of FIG. 1 which is exploded in detail.

FIG. 1 is a partly exploded three-dimensional schematic view of an ultrasonic scanhead according to an embodiment of the invention. FIG. 2 is a schematic cross-sectional view of the ultrasonic scanhead of FIG. 1 which is assembled. FIG. 3 is another schematic cross-sectional view of the ultrasonic scanhead of FIG. 1 which is assembled. FIG. 4 is a schematic three-dimensional view of the ultrasonic scanhead of FIG. 1 which is exploded in detail. FIG. 5 is another schematic three-dimensional view of the ultrasonic scanhead of FIG. 1 which is exploded in detail. Referring to FIG. 1 to FIG. 5, the ultrasonic scanhead 200 of an embodiment includes an encoder 210, a pivot 220, a voice coil motor 230, a transducer 240, an outer cover 250, a connecting element 260, a base 270, a first circuit board 280 and a second circuit board 290.

The outer cover 250 includes an outer cover body 252 and a front cover 254. The outer cover body 252 includes a top cover 252a, a bottom cover 252b and a back cover 252c. A front edge of the top cover 252a and a front edge of the bottom cover 252b form an opening 252d. A rear edge of the top cover 252a and a rear edge of the bottom cover 252b form another opening 252e. The front cover 254 is disposed at the opening 252d of the outer cover body 252, and the back cover 252c is disposed at the other opening 252e of the outer cover body 252. In addition, the base 270 is fixed within the outer cover body 252 of the outer cover 250.

Figure 6:
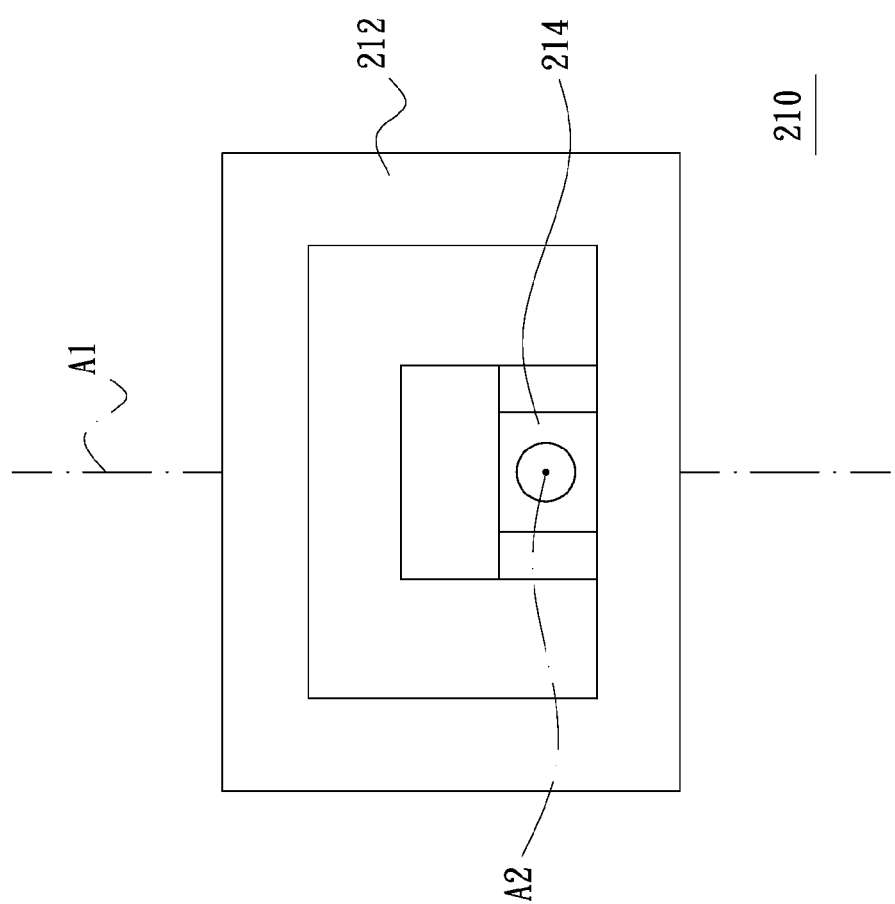
FIG. 6 is a schematic front view of the encoder of FIG. 4.

FIG. 6 is a schematic front view of the encoder of FIG. 4. Referring to FIG. 1 to FIG. 6, the encoder 210 is disposed at the base 270 and located within the outer cover body 252 of the outer cover 250. The encoder 210 includes a fixed element 212 and a rotary element 214. The fixed element 212 is fixed to the base 270. The rotary element 214 is rotatably disposed at the fixed element 212 and capable of rotating about a first axis A1. The first circuit board 280 is disposed on the base 270 and the encoder 210 is electrically connected to the first circuit board 280.

Figure 7:
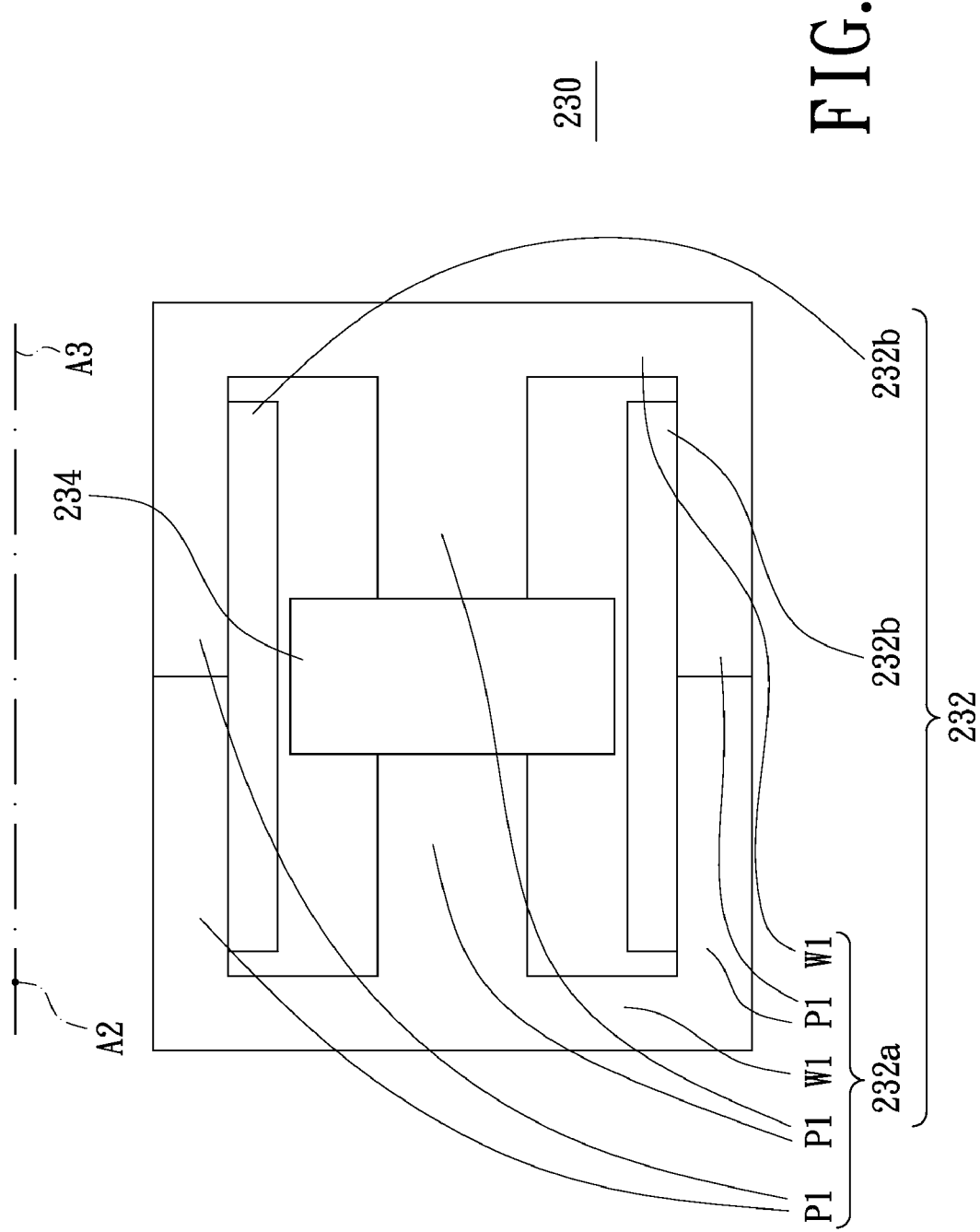
FIG. 7 is a schematic front view of the voice coil motor of FIG. 4 which is assembled.

FIG. 7 is a schematic front view of the voice coil motor of FIG. 4 which is assembled. Referring to FIG. 1 to FIG. 5 and FIG. 7, the voice coil motor 230 is disposed on the base 270 and located within the outer cover body 252 of the outer cover 250. The voice coil motor 230 includes a stator 232 and a mover 234. The stator 232 includes an iron block 232a and two magnetic blocks 232b. The iron block 232a has two sidewalls W1 and a plurality of pairs of connecting plates P1. The connecting plates P1 are located between the sidewalls W1. One of the pairs of the connecting plates P1 passes through mover 234. Each of the magnetic blocks 232b is disposed between two adjacent pairs of the connecting plates P1. The magnetic blocks 232b are respectively located at opposite sides of the mover 234. The mover 234 is, for example, a coil and is electrically connected to the first circuit board 280. The mover 234 is capable of moving linearly along a third axis A3 perpendicular to the first axis A1 and moving relatively to the stator 232.

Figure 8A:
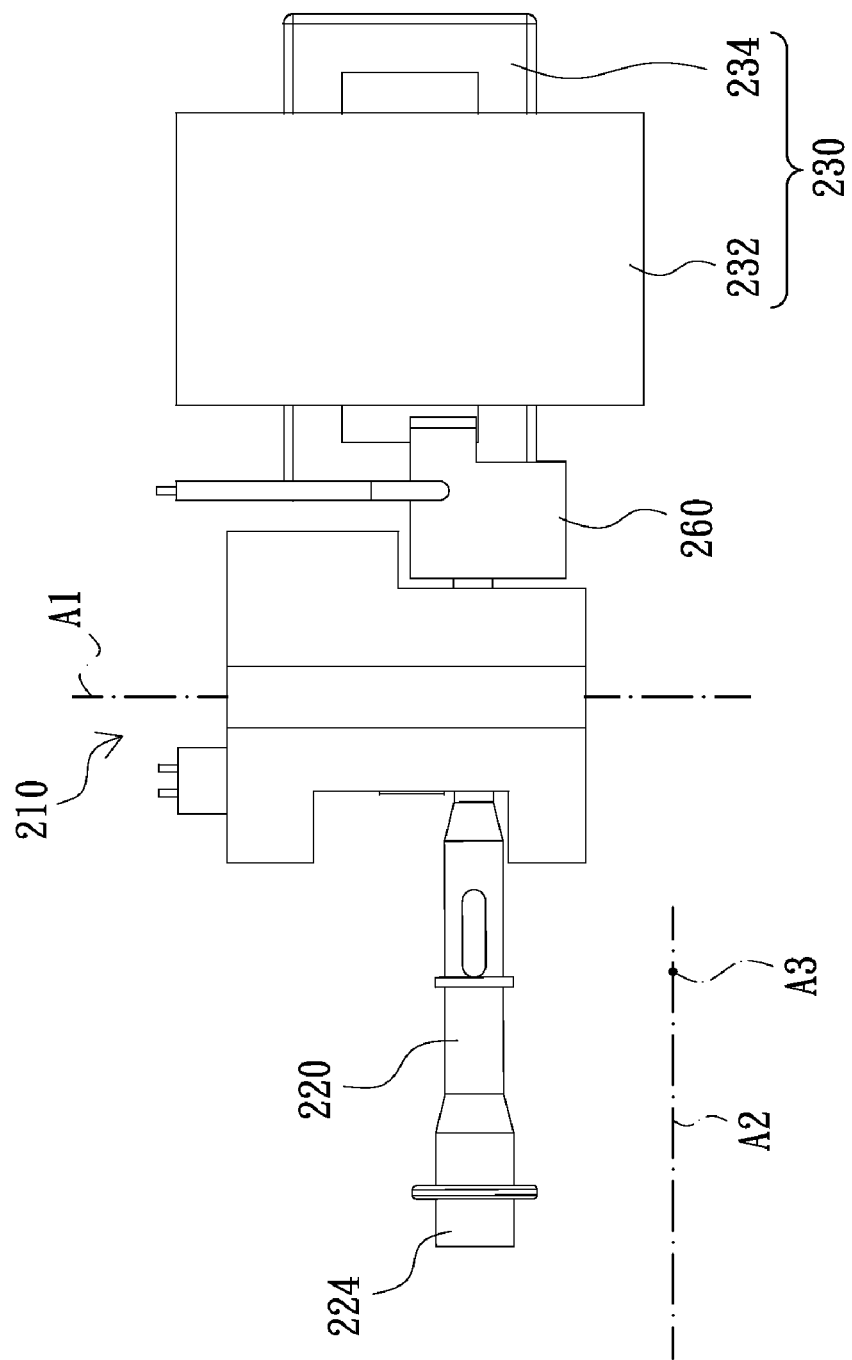
FIG. 8A is a schematic side view of the pivot, the encoder, the connecting element and the voice coil motor of FIG. 4 which are assembled.
Figure 8B:
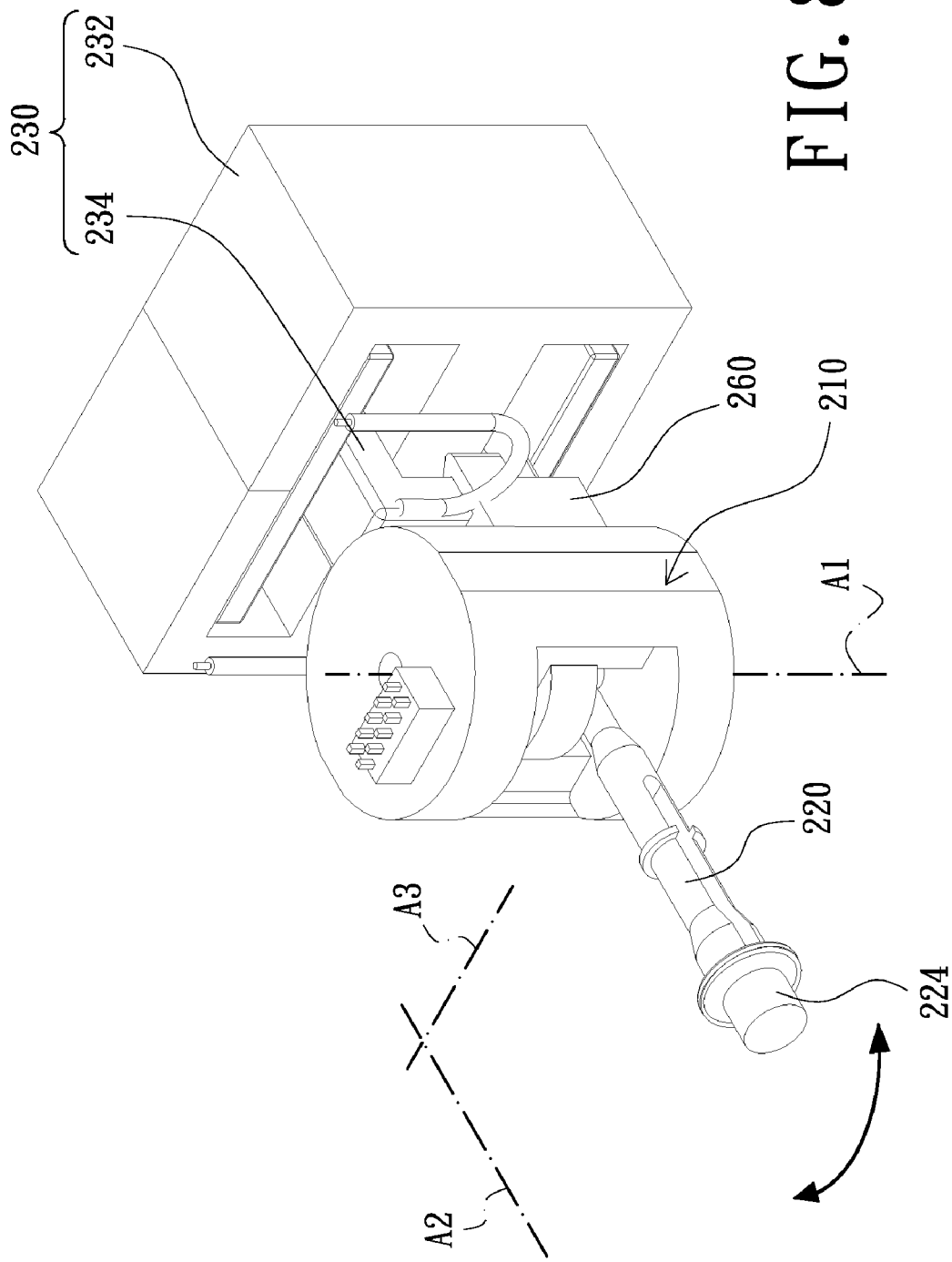
FIG. 8B is a schematic three-dimensional view of the pivot, the encoder, the connecting element and the voice coil motor of FIG. 4 which are assembled.

FIG. 8A is a schematic side view of the pivot, the encoder, the connecting element and the voice coil motor of FIG. 4 which are assembled. FIG. 8B is a schematic three-dimensional view of the pivot, the encoder, the connecting element and the voice coil motor of FIG. 4 which are assembled. Referring to FIG. 2 to FIG. 6, FIGS. 8A and 8B, the pivot 220 is disposed within the outer cover 250. The pivot 220 passes through the rotary element 214 of the encoder 210 and is capable of rotating with the rotary element 214. The pivot 220 extends along a second axis A2 and has a first end 222 and a second end 224 opposite to the first end 222. Furthermore, the second axis A2 is perpendicular to the first axis A1 and the third axis A3.

The first end 222 of the pivot 220 is connected to the connecting element 260 and the connecting element 260 clasps the mover 234 of the voice coil motor 230. The transducer 240 is disposed at the second end 224 of the pivot 220 and located within the front cover 254 of the outer cover 250. The transducer 240 is capable of emitting an ultrasonic wave. In an embodiment, the transducer 240 is detachably disposed at the second end 224 of the pivot 220. For example, the transducer 240 includes a screw thread (not shown), and the second end 224 of the pivot 220 includes another screw thread corresponding to the screw thread of the transducer 240. The transducer 240 is capable of being fixed to the second end 224 of the pivot 220 via the screw thread of the transducer 240 by means of a rotation manner. In another embodiment of the invention, the transducer 240 includes a clasping structure (not shown), and the second end 224 of the pivot 220 includes another clasping structure corresponding to the clasping structure of the transducer 240. The transducer 240 is capable of being fixed to the second end 224 of the pivot 220 by means of a clasping manner.

In this embodiment, because the pivot 220 passes through the encoder 210, as compared to the conventional art, the size of the ultrasonic scanhead 200 of this embodiment is relatively small. In addition, because the transducer 240 of the ultrasonic scanhead 200 of the embodiment is detachably disposed at the second end 224 of the pivot 220, as compared to the conventional art, it is convenient for a user to make a replacement for the transducer 240 of the ultrasonic scanhead 200 of the embodiment. Therefore, the cost of the replacement is decreased and the way of the replacement is simple and easy. In other words, there is no need to make an entire replacement for the ultrasonic scanhead 200.

The second circuit board 290 is disposed on the base 270 and opposite to the first circuit board 280. The transducer 240 is electrically connected to the second circuit board 290 by a wire through the interior of the pivot 220. The first circuit board 280 and the second circuit board 290 are electrically connected to a cable B1 through a plurality of wires (not shown). The cable B1 is electrically connected to a computer system (not shown) so that the user is able to control the operation of the ultrasonic scanhead 220 by means of the computer system.

When the ultrasonic scanhead 200 is operated, the mover 234 of the voice coil motor 230 reciprocates along the third axis A3 for driving the pivot 220 to oscillate back and forth so that the rotary element 214 of the encoder 210 rotates back and forth about the first axis A1. Meanwhile, the transducer 240 transmits ultrasonic impulse signals into an object and receives ultrasonic impulse signals reflected from the object. Therefore, the computer system is capable of transforming related signals into an image displayed on a display device by means of the ultrasonic impulse signals received by transducer 240 and angle position variation signals generated by the encoder 210 during reciprocating oscillation of the pivot 220.

In the embodiment, the voice coil motor 230 of the ultrasonic scanhead 200 drives the pivot 220 to oscillate back and forth, as compared to the conventional art, the voice coil motor 230 operates smoothly without force ripple and cogging force.

According to the mentioned above, the embodiment or the embodiments of the invention may have at least one of the advantages:

1. In the embodiment of the invention, because the pivot of the ultrasonic scanhead passes through the encoder, as compared to the conventional art, the size of the ultrasonic scanhead of the embodiment of the invention is relatively small.

2. In this embodiment of the invention, because the voice coil motor of the ultrasonic scanhead drives the pivot to oscillate back and forth, as compared to the conventional art, the voice coil motor operates smoothly without force ripple and cogging force.

3. In the embodiment of the invention, because the transducer of the ultrasonic scanhead is detachably disposed at the second end of the pivot, as compared to the conventional art, it is convenient for a user to make a replacement for the transducer of the ultrasonic scanhead of the embodiment of the invention.

The foregoing description of the preferred embodiment of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like is not necessary limited the claim scope to a specific embodiment, and the reference to particularly preferred exemplary embodiments of the invention does not imply a limitation on the invention, and no such limitation is to be inferred. The invention is limited only by the spirit and scope of the appended claims. The abstract of the disclosure is provided to comply with the rules requiring an abstract, which will allow a searcher to quickly ascertain the subject matter of the technical disclosure of any patent issued from this disclosure. It is submitted with the understanding that it will not be used to interpret or limit the scope or meaning of the claims. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims

What is claimed is:

1. An ultrasonic scanhead comprising:
   an encoder comprising a fixed element and a rotary element, wherein the rotary element is disposed at the fixed element and capable of rotating about a first axis;
   a pivot extending along a second axis, having a first distal end passing through both fixed and rotary elements of the encoder and a second distal end opposite to the first distal end, and capable of rotating with the rotary element;
   a voice coil motor comprising a stator and a mover, wherein the first distal end of the pivot is connected to the mover, and the mover is capable of moving linearly along a third axis and moving relatively to the stator, and the first axis, the second axis and the third axis are substantially perpendicular to each other; and
   a transducer disposed at the second distal end of the pivot and capable of emitting an ultrasonic wave.

2. The ultrasonic scanhead as claimed in claim 1, wherein the transducer is detachably disposed at the second distal end of the pivot.

3. The ultrasonic scanhead as claimed in claim 2, wherein the transducer comprises a screw thread and the transducer is fixed to the second distal end of the pivot via the screw thread.

4. The ultrasonic scanhead as claimed in claim 1, further comprising an outer cover, wherein the outer cover comprises an outer cover body and a front cover, and the encoder, the pivot, the voice coil motor, and the transducer are disposed in the outer cover, the front cover is disposed at an opening of the outer cover body, and the transducer is located within the front cover.

5. The ultrasonic scanhead as claimed in claim 1, further comprising a connecting element, wherein the first distal end of the pivot is connected to the connecting element and the connecting element clasps the mover.

* * * * *